(12) United States Patent
Lou et al.

(10) Patent No.: US 10,575,749 B2
(45) Date of Patent: Mar. 3, 2020

(54) DETECTING CONDUCTION TIMING

(71) Applicant: CARDIOINSIGHT TECHNOLOGIES, INC., Independence, OH (US)

(72) Inventors: Qing Lou, Powell, OH (US); Meredith E. Stone, Strongsville, OH (US); Qingguo Zeng, Solon, OH (US); Jeffrey B. Adair, Cuyahoga Falls, OH (US); Connor S. Edel, Independence, OH (US); Ping Jia, Solon, OH (US); Kevin R. Ponziani, Rocky River, OH (US); Brian P. George, Cleveland, OH (US); Ryan M. Bokan, Cleveland, OH (US); Matthew J. Sabo, Independence, OH (US); Vladimir A. Turovskiy, Strongsville, OH (US); Ketal C. Patel, Independence, OH (US); Charulatha Ramanathan, Solon, OH (US)

(73) Assignee: CARDIOINSIGHT TECHNOLOGIES, INC., Independence, OH (US)

(*) Notice: Subject to any disclaimer, the term of this patent is extended or adjusted under 35 U.S.C. 154(b) by 211 days.

(21) Appl. No.: 15/498,662

(22) Filed: Apr. 27, 2017

(65) Prior Publication Data

US 2017/0319089 A1    Nov. 9, 2017

Related U.S. Application Data

(60) Provisional application No. 62/331,116, filed on May 3, 2016.

(51) Int. Cl.
*A61B 5/0468* (2006.01)
*A61B 5/0432* (2006.01)
(Continued)

(52) U.S. Cl.
CPC ............ *A61B 5/0468* (2013.01); *A61B 5/044* (2013.01); *A61B 5/0432* (2013.01); *A61B 5/0472* (2013.01); *A61B 5/7203* (2013.01)

(58) Field of Classification Search
CPC .................... A61B 5/0468; A61B 5/04012
(Continued)

(56) References Cited

U.S. PATENT DOCUMENTS

| 2012/0184863 | A1 | 7/2012 | Harlev |
| 2014/0371609 | A1 | 12/2014 | Narayan |
| 2015/0216438 | A1 | 8/2015 | Bokan et al. |

FOREIGN PATENT DOCUMENTS

| WO | 2012/037471 A2 | 3/2012 |
| WO | 2015/073962 A1 | 5/2015 |

OTHER PUBLICATIONS

International Search Report with Written Opinion for Application No. PCT/US2017/029267 dated Jul. 13, 2017.
(Continued)

*Primary Examiner* — Nadia A Mahmood
(74) *Attorney, Agent, or Firm* — Tarolli, Sundheim, Covell & Tummino LLP

(57) ABSTRACT

An example method includes analyzing morphology and/or amplitude of each of a plurality of electrophysiological signals across a surface of a patient's body to identify candidate segments of each signal satisfying predetermined conduction pattern criteria. The method also includes determining a conduction timing parameter for each candidate segment in each of the electrophysiological signals.

21 Claims, 8 Drawing Sheets

(51) Int. Cl.
*A61B 5/044* (2006.01)
*A61B 5/0472* (2006.01)
*A61B 5/00* (2006.01)

(58) Field of Classification Search
USPC .......................................................... 600/516
See application file for complete search history.

(56) References Cited

OTHER PUBLICATIONS

Ioan Liuba, et al., "Activation mapping of focal atrial tachycardia: the impact of the method for estimating activation time", Journal of Interventional Cardiac Electrophysiology, Kluwer Academic Publishers, BO, vol. 26, No. 3, Oct. 29, 2009 (Oct. 29, 2009), pp. 169-180.

Carl F. Pieper, et al., "Activation Time Detection Algorithms Used in Computerized Intraoperative Cardiac Mapping: A Comparison with Manually Determined Activation Times", Journal of Cardiovascular Electrophysiology., vol. 2, No. 5, 1 Oct. 1, 1991 (Oct. 1, 1991), pp. 388-397.

M.J.M. Cluitmans, et al., "Noninvasive reconstruction of cardiac electrical activity: update on current methods, applications and challenges", Netherlands Heart Journal, vol. 23, No. 6, Apr. 21, 2015 (Apr. 21, 2015), pp. 301-311.

Ironi Liliana, et al., "Interplay of spatial aggregation and computational geometry in extracting diagnostic features from cardiac activation data", Computer Methods and Programs in Biomedicine, vol. 107, No. 3, Jan. 1, 2012 (Jan. 1, 2012), pp. 456-467.

C.D. Cantwell, et al., "Techniques for automated local activation time annotation and conduction velocity estimation in cardiac mapping", Computers in Biology and Medicine., vol. 65, Apr. 25, 2015 (Apr. 25, 2015), pp. 229-242.

DETECTING CONDUCTION TIMING

CROSS-REFERENCE TO RELATED APPLICATION

This application claims the benefit of U.S. provisional patent application No. 62/331,116 filed on May 3, 2016, and entitled DETECTING CONDUCTION TIMING, which is incorporated herein by reference in its entirety.

TECHNICAL FIELD

This disclosure relates to detecting conduction timing and corresponding patterns thereof.

BACKGROUND

Existing approaches to extract the activation temporal information from electrograms may involve (1) aggressively filtering the virtual electrogram to remove noise, and (2) identifying the zero-crossings of filtered signals at the downward slopes as the local activation time. The disadvantage of this existing approach is that the aggressive filtering, while removing noise, may also filter out part of the signal, and therefore leading to loss of information and distortion of the downward slopes in the electrogram. In addition, the zero-crossing of electrograms, which serves as a surrogate of the activation time, may not be a robust measure in the presence of noise (e.g., baseline drifting) during the body-surface recordings.

SUMMARY

This disclosure relates to detecting conduction timing.

As one example, a method includes analyzing morphology and/or amplitude of each of a plurality of electrophysiological signals across a surface of a patient's body to identify candidate segments of each signal satisfying predetermined conduction pattern criteria. The method also includes determining a conduction timing parameter for each candidate segment in each of the electrophysiological signals. In some examples, one or more non-transitory computer-readable media stores instructions is programmed to perform the method.

As another example, a system includes memory to store machine readable instructions and data. The data includes electrical data representing electrophysiological signals distributed across a body surface. One or more processors access the memory and execute the instructions. The instructions include a conduction pattern estimator that analyzes morphology and/or amplitude of each of a plurality of electrophysiological signals across a surface of a patient's body to identify candidate segments of each of the plurality of signals that satisfy predetermined conduction pattern criteria. A conduction pattern parameter identifier determines a conduction timing parameter for each of the identified candidate segments in the electrophysiological signals. An output engine provides output data to drive a display with a graphical map that includes a visualization of or derived from the conduction timing parameters determined for the electrophysiological signals.

DETAILED DESCRIPTION

Figure 1:
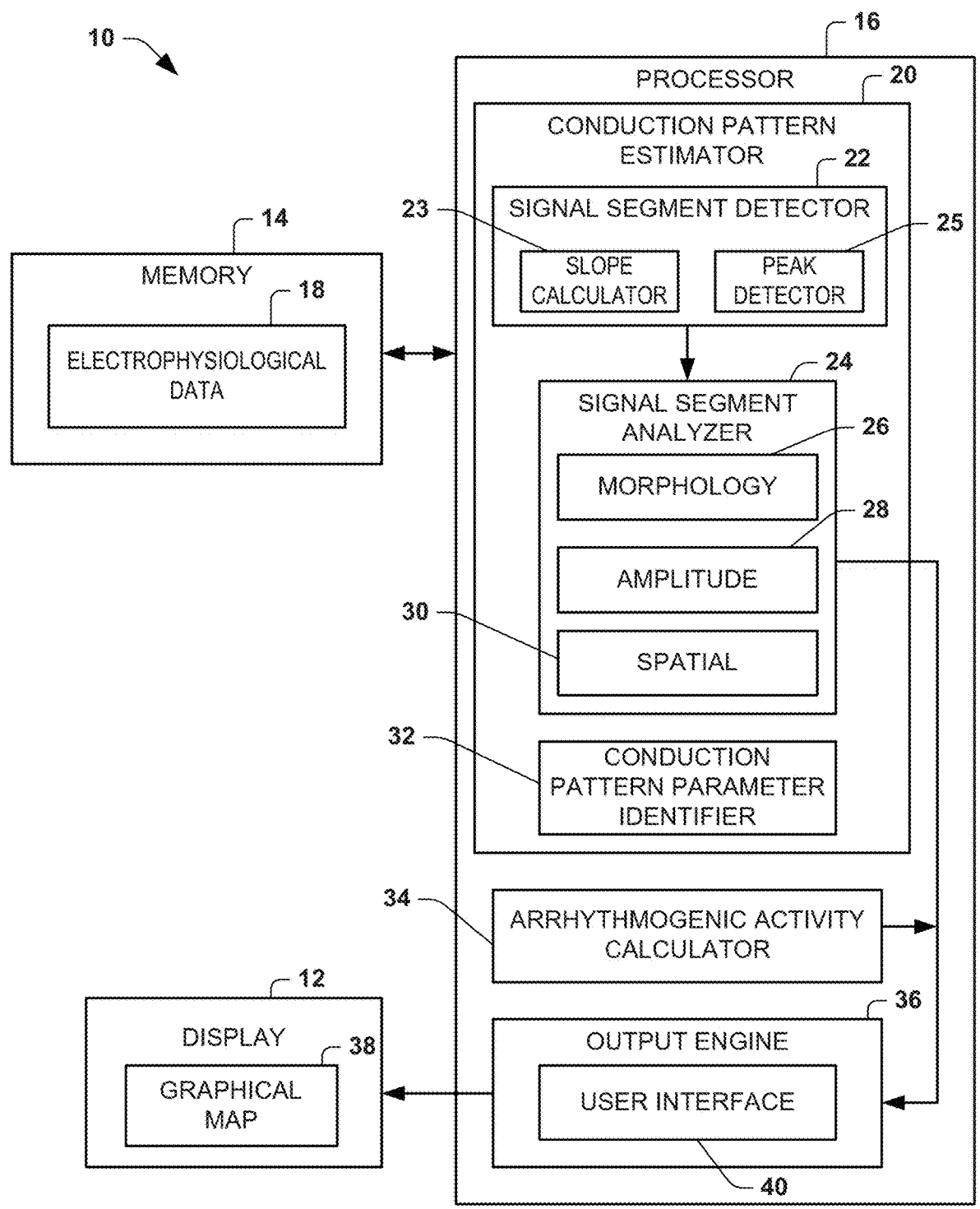
FIG. 1 depicts an example of a system to estimate conduction of patterns from electrophysiological data.

This disclosure relates to detecting conduction timing, such as activation time and corresponding conduction patterns or sequences in electrical signals distributed across a surface (e.g., an exterior or interior surface of) a patient's body. This disclosure also provides a visualization (e.g., a graphical user interface (GUI)) based on detected conduction patterns that can be utilized to provide an interactive graphical map.

As one example, systems and methods are provided to detect a conduction timing from electrophysiological signals, such as can be stored in memory as electrical data representing electrograms that have been reconstructed for a cardiac envelope (e.g., epicardial surface or another cardiac surface) or another surface of the patient's body (e.g., an external body surface).

As an example, the detection can include analyzing morphology and/or amplitude of each of a plurality of electrophysiological signals to determine candidate segments of each signal satisfying predetermined conduction pattern criteria (e.g., slope and amplitude criteria). The electrophysiological signals may include a set of electrogram distributed across a surface of a patient's body. Another portion of downward sloping segments of each of the signals that do not satisfy all the predetermined conduction pattern criteria can be designated as potential (or questionable) segments for further evaluation. Such further evaluation of the potential segments can include determining if each of the potential segments of the electrophysiological signals is spatially and temporally consistent with neighboring segments that had already been selected as one of the candidate segments. A respective segment that has been designated as a potential segment can be removed from further consideration if it is determined that it is not spatially and/or temporally consistent with neighboring candidates. Such spatial and temporal consistency across the surface can indicate the presence of a conduction pattern, thereby verifying whether or not a potential segment contains an activation time that is spatially and temporally linked with an identifiable conduction pattern. The candidate segments for each of the plurality of signals can be aggregated together and a conduction pattern parameter be identified for each candidate segment, such as corresponding to a consistently selected point along the segment (e.g., a fixed percentage of the peak-to-valley segment amplitude). The conduction pattern parameter can include activation time for each candidate sequence, which can be combined to determine a sequence of activation times across the cardiac envelope.

The approach herein is particularly robust for analysis of electrical activity that occurs during abnormal rhythms (arrhythmogenic activity). For example, non-invasive mapping may be employed to compute reconstructed electrograms on the cardiac envelope (e.g., the outer surface of the heart) from body-surface electrical measurements. Each electrogram contains the information of activation and repolarization at each location of the cardiac envelope (atria or ventricle). On the other hand, manually reviewing the electrograms does not easily reveal a conduction pattern. This is especially true when reviewing the arrhythmia data, where the conduction is complex but the understanding of the complex conduction is urgently needed.

This disclosure thus facilitates identifying the conduction patterns from electrograms. The conduction pattern revealed during abnormal rhythms can then enable diagnosis and treatment of the electrical dysfunction of the heart. The conduction pattern can be detected while avoiding signal distortion due to aggressive filtering, as well as does not require any phase calculation. Thus, the approach herein is thus capable of analyzing electrograms with shorter duration. As a result, systems and methods disclosed herein can further enhance the accuracy of our non-invasive mapping, which would lead to better clinical outcomes.

As a further example, this disclosure includes an interactive graphical user interface (GUI) that provides a visualization scheme for arrhythmogenic drivers that highlights arrhythmogenic activity (e.g., rotations and/or focal points) in a color map. The GUI further enables a user to select a driver, and review and ignore individual contributing drivers within a single map, for example. The GUI implements a filtering mechanism on the driver map that allows the user to view un-reviewed, final, or all drivers, for example.

FIG. 1 depicts an example of a system 10 that can be utilized to determine conduction patterns as well as to generate graphical maps 38 that can be visualized on a display 12. The system 10 includes memory 14, which can include one or more non-transitory machine-readable media that stores instructions and data. The system 10 also includes a processor 16, which can include one or more processing cores, to access the memory and execute corresponding instructions demonstrated within the processor block 16.

In the example of FIG. 1, the memory stores electrophysiological data 18. The electrophysiological data can correspond to unipolar electrograms or other electrophysiological signals that can be measured or estimated based upon measured or electrical activity across the surface of a patient's body. For example, the electrophysiological data 18 can correspond to electroanatomical data that has been reconstructed onto a cardiac envelope of the patient's heart by solving the inverse problem with respect to electrical signals measured non-invasively across a surface of a patient's body, such as the patient's thorax or a portion thereof. Examples of sensors that may be utilized to acquire the body surface electrical activity are disclosed in U.S. Pat. No. 9,549,683 and International application No. PCT/US20091063803.

These and other various measurement systems can be utilized to acquire the body surface electrical measurements non-invasively that can be utilized to provide the electrophysiological data 18 that can either correspond to live data that is acquired intraprocedurally, or the electrophysiological data 18 can correspond to data that has been acquired a priori and stored in the memory 14, such as part of a previous electrophysiology (EP) study or acquired during another intervention. Each of the signals in the electrophysiological data 18 represent the electrical signals at nodes spatially distributed across a surface (e.g., body surface or cardiac surface envelope), and thus may include waveform information and geometry information for the nodes in two- or three-dimensional space.

The processor 16 executes machine readable instructions that include a conduction pattern estimator 20. The conduction pattern estimator 20 is programmed to identify the conduction pattern parameter (e.g., corresponding to an activation time) for selected segments of each of the electrophysiological signals represented by the data 18. As mentioned, electrophysiological data 18 can correspond to a plurality of points distributed across a surface, such as an anatomical surface or an envelope having a known geometry with respect to an anatomical structure.

In the example of FIG. 1, the conduction pattern estimator 20 includes a signal segment detector 22. The signal segment detector 22 is used to detect segments of signal waveforms having a morphology known to be consistent with the conduction timing parameter of interest. In some examples, the pattern estimator 20 suggests a set of potential segments and the user selects a portion of suggested segments for evaluation in response to a user input via GUI. Thus the user can either continue with evaluating the selected portion of the segments for calculating conduction timing and other parameters or provide a user input to discard them, such as by tagging the data with information to enable such data to be ignored.

For sake of consistency and ease of explanation, the conduction timing parameter of interest is disclosed herein mainly as an activation time parameter. In other examples, the conduction timing parameter may represent other temporal parameters that occur repeatedly over time in an electrophysiological signal of interest over time, such as providing an indication of a repolarization time or a relative activation and repolarization time.

As one example, the signal segment detector 22 includes a slope calculator 23 and a peak detector 25. The slope calculator 23 computes the slope of segments of each the signal waveforms. The peak detector 25 identifies points along the signal waveforms corresponding to peaks, which include positive peaks as well as negative peaks (troughs). For instance, the peak detector 25 identifies peaks as points that change from positive slope to negative slope or from negative slope to positive slope, such as determined as the time-based derivative of the computed slope. The signal segment detector 22 utilizes the computed slope and peaks to identify signal segments having a downward slope that is potentially associated with an activation (referred to as "downward sloping segments"). Each downward sloping segment thus can be defined by a portion of a given signal waveform determined to have a negative slope and extends between a detected peak and trough of the given signal. The downward sloping segment may be substantially linear or non-linear (curved).

A signal segment analyzer 24 analyzes each of the detected signal segments (e.g., downward sloping segments detected by detector 22) to identify segments that the system 10 is to consider as true activations. For example, the signal segment analyzer 24 can include a morphology analysis component 26 and an amplitude analysis component 28. The signal segment analyzer 24 thus can select a portion of the candidate segments from the detected signal segments based on the morphology and amplitude components 26 and 28 ascertaining that the amplitude and duration of the signals satisfy certain criteria (e.g., a sufficiently large amplitude and sufficiently short duration). The downward sloping segments satisfying such morphology and amplitude criteria can be stored in memory 14 as candidate data representing a set of candidate segments.

The signal segment analyzer 24 can employ a spatial analysis component 30 to evaluate the remaining set of the detected signal segments that did not satisfy the morphology and amplitude criteria applied by components 26 and 28. The set of remaining signal segments may be referred to as potential candidate segments. For instance, the spatial analysis component 30 can analyze each of the questionable signal segments relative to one or more neighboring candidate segments at nodes located near (e.g., within a predetermined distance from) the node location for each respective questionable signal segment and within a time window of the time interval that defines the segment. The time window may be fixed or vary as a function the distance between the nodes being evaluated. The spatial analysis component 30 thus can determine if each questionable signal segment has one or more neighbor nodes that have been determined (e.g., by morphology and amplitude components 26, 28) to exhibit activation at a sufficiently high level of confidence within a time window of the respective questionable segment. That is, if a given signal segment exhibits activation at a particular location on the surface, there should be one or more neighboring signal segments exhibiting activation that are spatially and temporally consistent with the given signal segment. Consequently, candidate signal segments that have been determined to exhibit an activation (e.g., based upon morphology and amplitude components 26 and 28) can be used by the signal segment analyzer 24 to confirm whether or not questionable signal segments at neighboring should be discarded as noise or be considered as including a true activation time.

By way of example, if no neighboring signal segments have been determined to exhibit activation time, then the questionable signal segments can be discarded. If neighboring signal segments exhibit an activation time within a time window of a given questionable signal segments, there is an increased likelihood that the given questionable signal segment likewise exhibits an activation time and thus can be designated (by the spatial analysis component 30) as another candidate segment. The set of candidate segments determined by the spatial analysis component 30 and the set of candidate segments determined by the morphology and amplitude components 26 and 28 can be aggregated together to provide an aggregate set of candidate segments that exhibit activation time. The aggregate set of candidate segments can be stored in memory 14.

The conduction pattern estimator 20 also includes a conduction pattern parameter identifier 32 to determine a conduction parameter for each candidate segment that has been identified. As disclosed herein, the conduction pattern parameter identifier 32 can calculate the activation time as a point in time within the time interval for each of the candidate signal segments. For example, the identifier 32 can determine the activation time as any point around the downward sloping segment that is consistently selected from each downward sloping candidate signal segment. As one example, the identifier 32 can designate the activation time as the point in time when the signal reaches one-half of the amplitude between the peak and trough in the downward sloping signal segment (i.e., 50% of the downward slope). Of course any percentage of the amplitude could be used.

Figure 2:
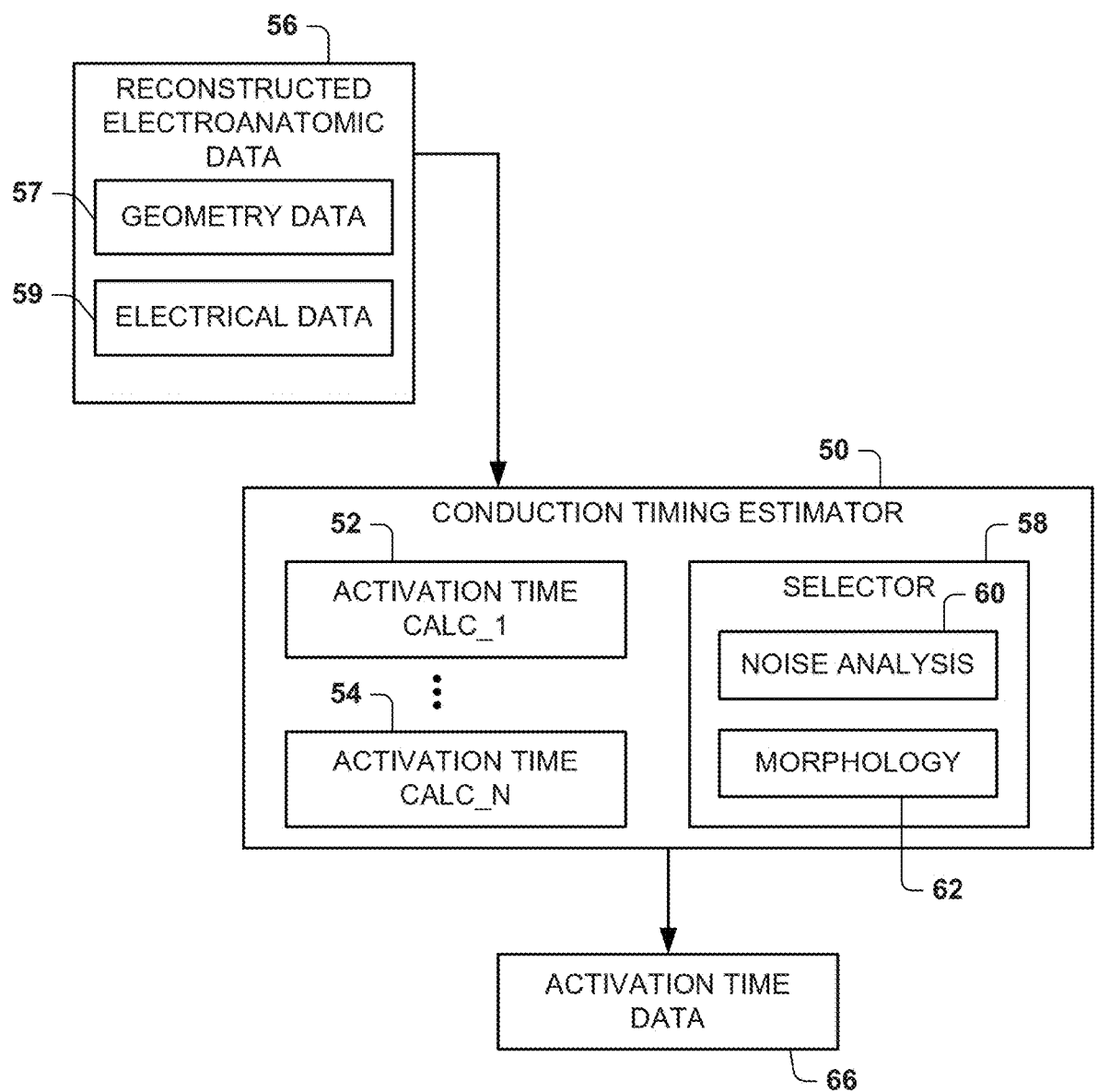
FIG. 2 depicts an example of a dynamic activation time estimator that can utilize conduction pattern estimation from FIG. 1.

In some examples depending upon noise or signal morphology, as disclosed herein with respect to FIG. 2, the conduction pattern parameter identifier 32 can compute the activation time according to one or more different approaches. For instance, the conduction pattern identifier 32 can be programmed to calculate the maximum derivative of the negative slope of the candidate segment or, in other examples, as the zero crossing point of the negative sloping candidate segment. The activation time that is determined by the pattern identifier 32 for each candidate signal segment can be stored in memory 14, such as corresponding to a time indexed indication with respect to each of the plurality of signals represented by the data 18.

As a further example, the processor 16 can include instructions corresponding to an arrhythmogenic activity calculator 34. The arrhythmogenic activity calculator 34 can be programmed to characterize the electrophysiological data 18 across the surface. Some specific examples of the types and forms arrhythmogenic drivers that the arrhythmogenic activity calculator 34 can compute include rotations, trajectories of rotations, wave front lines, focal sources and focal sustainability. Further examples on computing such arrhythmogenic drivers are disclosed in U.S. Pat. Pub. 2014/0336520, corresponding to U.S. application Ser. No. 14/273,458, filed May 8, 2014, and entitled ANALYSIS AND DETECTION FOR ARYTHMIA DRIVERS, which is incorporated herein by reference. Further examples of other types of calculations that can be computed by the arrhythmogenic activity calculator 34 and provide related visualizations to the display 12 are disclosed in International Publication No. WO2014/113555, filed Jan. 16, 2014, and entitled FOCAL POINT IDENTIFICATION AND MAPPING, and in International Publication No. WO2014/113672, filed Jan. 17, 2014, and entitled WAVE FRONT DETECTION FOR ELECTROPHYSIOLOGICAL SIGNALS, each of which publications is incorporated herein by reference.

An output engine 36 can be utilized to generate one or more graphical maps 38 that can be presented on the display 12. For example, the output engine can generate an activation map based on the activation times determined by the conduction pattern estimator 20. This can be for a selected set of the signals distributed across the surface or for the entire surface and for one or more time intervals of interest, which can be selected in response to a user input. Examples of the types of output visualizations and maps that can be generated are disclosed herein (see, e.g., FIGS. 6, 7 and 8) as well as those disclosed in the above-incorporated U.S. Pat. Pub. 2014/0336520, International Publication No. WO2014/113672 and/or International Publication No. WO2014/113672.

As disclosed herein, in some examples, the electrophysiological data 18 is spatially and temporally consistent across the entire cardiac surface such that a conduction pattern (activation) map can be generated for the entire cardiac surface over one or more time intervals. Similarly, the arrhythmogenic activity that is determined by the calculator 34 can also be temporally and spatially consistent such that the resulting graphical map of the cardiac activity can be superimposed on a graphical representation of a portion or the entire heart. The output engine 36 can also include a user interface that can be utilized to set parameters for the graphical map and to otherwise interact with and select portions of the electrophysiological data 18 in response to user input, such as disclosed herein.

FIG. 2 depicts an example of a dynamic activation time estimator 50 such as can utilize the conduction pattern estimator 20. For example, the dynamic activation time estimator 50 can include a plurality of instances of activation time calculators 52 through 54 demonstrated at Activation Time Calc_1 through Activation Time Calc_N, where N positive integer greater than or equal to 2. The estimator 50 thus can employ any activation time calculator 52 through 54 to compute activation time for the plurality of signals demonstrated as reconstructed electroanatomic data 56. Each of the activation time calculators 52 through 54 can implement a different calculation function for computing activation times. For example, one of the calculators is configured as the conduction pattern estimator 20 of FIG. 1, another of the calculators can implement a zero crossing detector and still another calculator computes a maximum derivative of the negative slope to determine activation time. Those skilled in the art thus will appreciate various functions that can be utilized to determine activation time for the signals represented by the electroanatomic data 56.

For example, reconstructed electroanatomic data 56 can be stored in memory and include both geometry data 57 and electrical data 59 for a cardiac envelope for which the signals have been reconstructed by solving the inverse problem based upon non-invasively measured electrical signals. Thus, for each of the plurality of signals distributed across the cardiac envelope for one or more time intervals, the estimator 50 can employ a selected one of the activation time calculators 52 through 54 for computing the activation time for each of the respective segments. A common activation time calculator can be used for each of the signals or different activation time calculators can be used to compute the activation time for different segments of the same signal location for different time segments.

The estimator 50 includes a selector 58 to select which of the activation time calculators 52 through 54 to utilize for computing the activation times for each given segment. For example, the selector 58 can include a noise analysis component 60 and a morphology analysis component 62, which can be programmed to analyze noise and morphology, respectively, of each of the signals. If the selector 58 otherwise ascertains that the signal exhibits a significant amount of noise (e.g., greater than a predetermined noise threshold), the selector 58 can selectively apply an activation time calculator 52 to filter the signal and apply a zero crossing detector or a maximum derivative of the negative slope for the potential candidate segment to determine the activation time. If the selector 58, based upon the noise analysis component 60 and/or the morphology analysis component 62, determines that the downward sloping segment has a sufficiently large amplitude (e.g., greater than an amplitude threshold) and a sufficient duration (e.g., having a duration that extends at least a minimum duration), the selector 58 can select a different activation time calculator 54. For example, where the selector components 60 and 62 determine that the downward sloping segment has a sufficient signal-to-noise ratio and exceeds a minimum threshold duration, the selector 58 can select one of the activation time calculators 52-54 corresponding to the conduction pattern estimator 20 disclosed with respect to FIG. 1. The estimator 50 can in turn generate an activation time data 66 that is stored in memory and be associated with the reconstructed electroanatomic data by being indexed with respect time.

Figure 3:
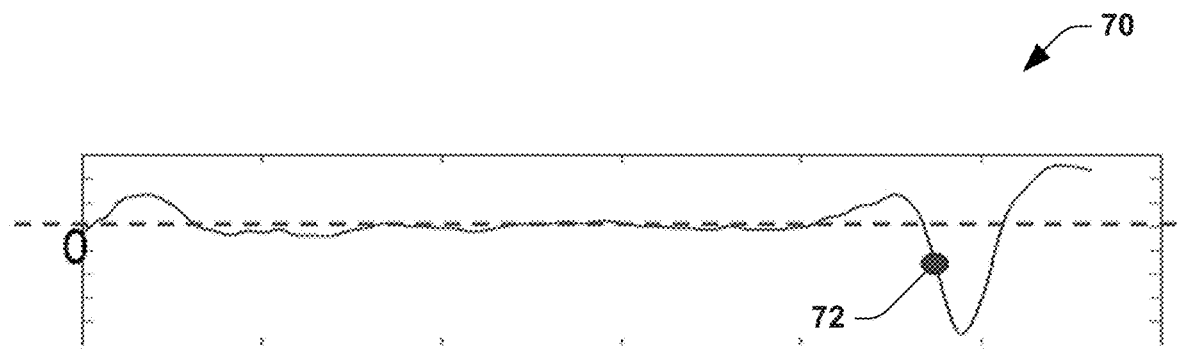
FIG. 3 depicts an example of a reconstructed electroanatomic signal.

FIG. 3 depicts an example of a signal 70 demonstrating a downward sloping portion that has been detected (by signal segment detector 22). Also shown in FIG. 3 is an activation time identified at 72 (identified by conduction pattern parameter identifier 32).

Figure 4:
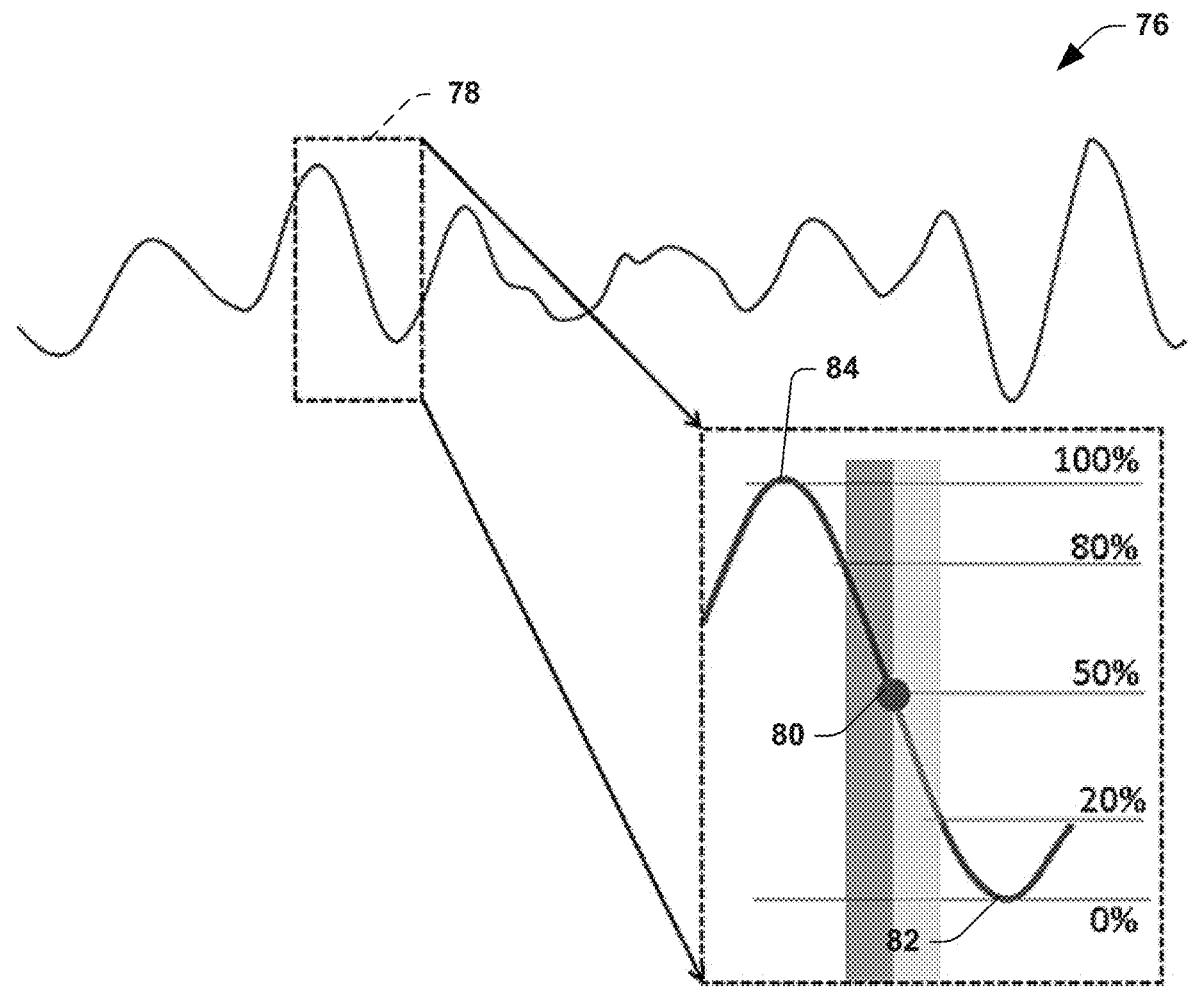
FIG. 4 depicts another electrogram signal demonstrating detection of activation time for a segment of such signal.
Figure 6:
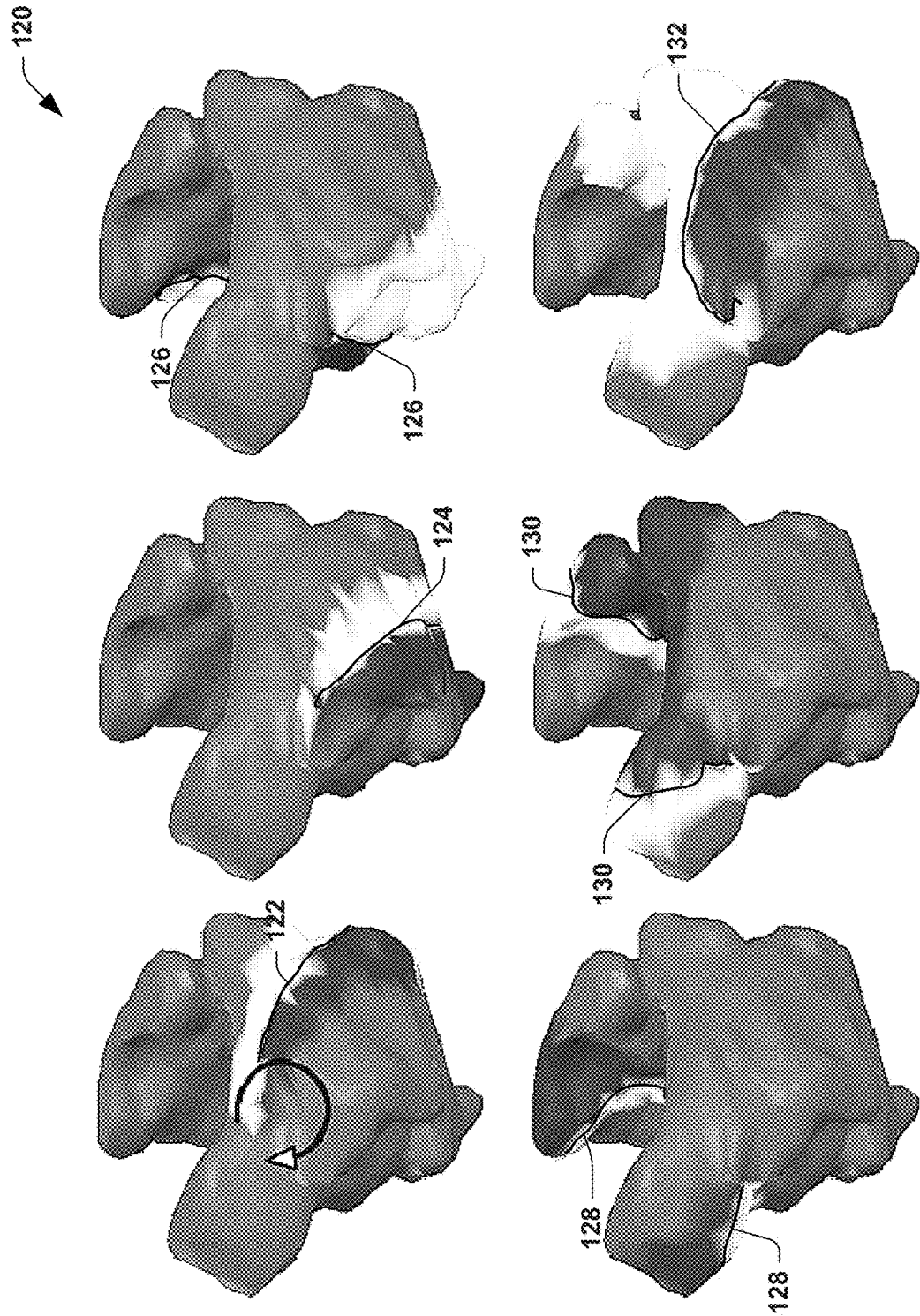
FIG. 6 depicts graphical maps demonstrating wave fronts during arrhythmogenic driver activity.

FIG. 4 demonstrates another signal 76 in which a selected portion of the signal demonstrated within a dotted box 78 is enlarged. The enlarged portion of the signal demonstrates an example where the activation time is determined at the 50% of the downward sloping segment, indicated at 80. This is at one-half of the amplitude between the peak and the trough 82 of the signal. Also demonstrated in the example of FIG. 4, a portion of the signal segment before and after the identified activation time can be selected to visualize a pre-activation time window for 80% to 50% of the segment as well as a post-activation time window from 50% to 20% of the amplitude relative to the identified activation time at 80. These pre and post-activation time windows thus can be visualized on a graphical map as regions extending along opposing sides of the activation wave front pattern, such as shown in FIG. 6.

Figure 5:
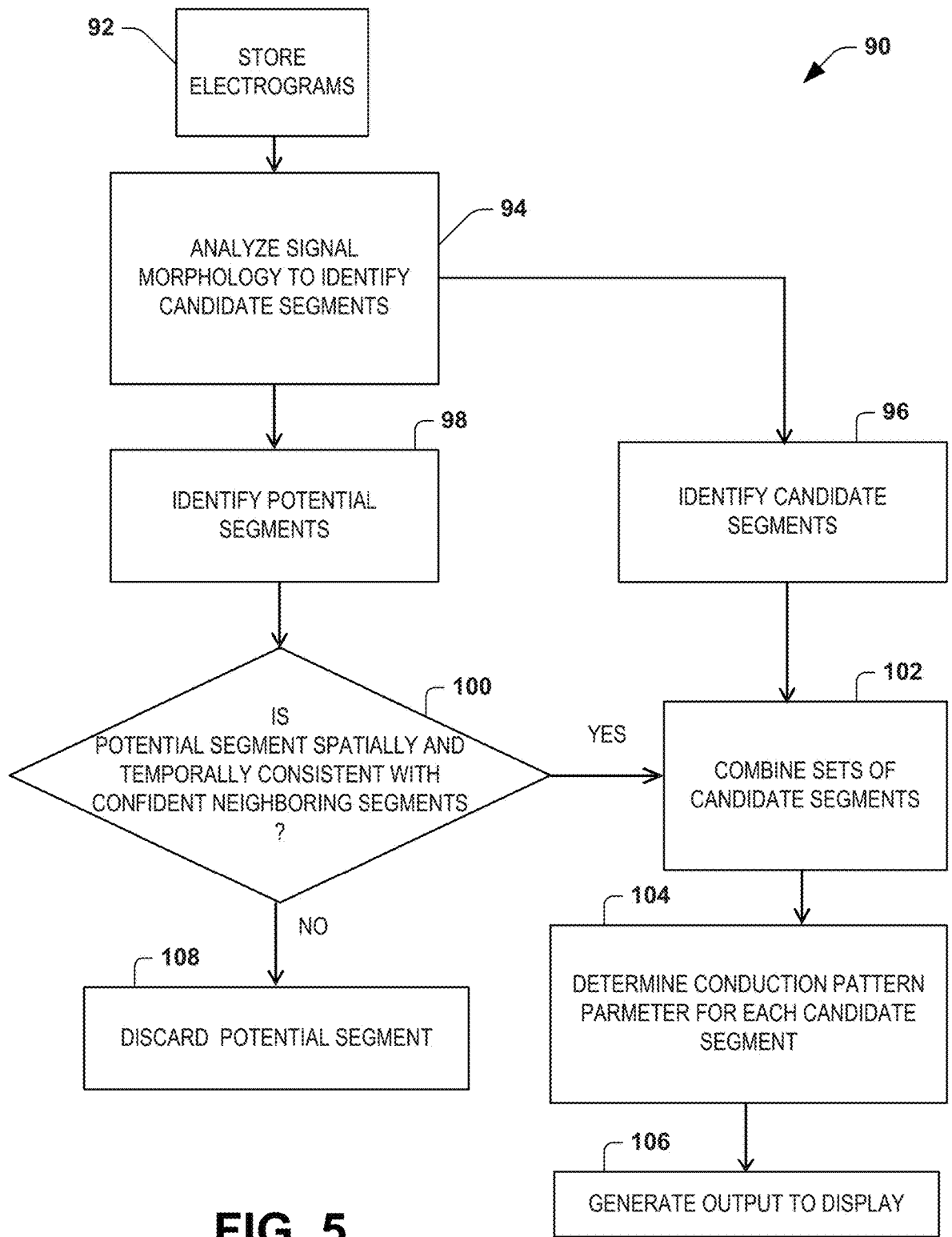
FIG. 5 is a flow diagram illustrating a method for detecting conduction patterns.

FIG. 5 is a flow diagram demonstrating an example method 90 to determine conduction patterns and conduction pattern parameters (activation times) for a plurality of electrophysiological signals (e.g., reconstructed electrograms). The method further can be implemented generate a corresponding output for visualization of one or more electrical characteristics of a patient's heart, including the conduction patterns and associated conduction pattern parameters. The method 90 begins at 92 in which electrograms (e.g., data 18, 56) are stored. The electrograms, for example, correspond to unipolar electrograms that have been reconstructed (e.g., by electrogram reconstruction 182) onto a cardiac envelope with respect to a patient's heart surface based on signals measured (e.g., by sensors 164) non-invasively across a patient's body, such as disclosed herein. At 94, signals are analyzed (e.g., by analyzer 24) to identify candidate signal segments. For example, morphology and amplitude of the signals can be analyzed to identify the candidate segments.

Candidate segments satisfying amplitude and duration criteria can be identified at 96. For example the candidates identified at 96 can define a set of downward sloping segments having a sufficiently large amplitude (e.g., exceeding an amplitude threshold) and short duration (e.g., less than a predetermined time interval) so that they can be considered confidently as exhibiting to conduction pattern activities, such as activation. At 98, downward sloping segments not meeting the requirements of large amplitude and short duration (per analysis at 96) or otherwise exhibiting significant amounts of noise can be identified (e.g., by analyzer 24) as potential segments. The method 90 thus first finds all the downward slopes that can be potentially associated with activation, and then puts all these downward slopes into two categories: one group of downward slopes that are associated with sufficiently large amplitude and short durations (based on applying amplitude and morphology criteria) and are considered as exhibiting true activation activity; and the other group, where the amplitude is small or contain noise, is defined as questionable slopes that could either due to damaged (but still functional) heart tissue or due to noise or far-field sensing.

The potential segments identified at 98 thus may define a set of questionable downward sloping segments requiring further analysis (e.g., by analyzer 24) at 100. For example, at 100, a determination is made whether each potential segment is spatially and temporally consistent with confident neighboring segments, namely those candidate segments identified at 96. That is, around a true activation at a particular location on the surface, there should be a neighboring activation happening at the same or similar time. In contrast, noise-associated slopes (due to its stochastic nature) are spatially isolated and therefore have low chance to have spatial continuity. If the determination at 100, by checking the neighborhood activation of for potential signal segments exhibiting questionable morphology, ascertains potential segments that do not have sufficient spatial continuity with neighboring nodes, the method proceeds to 108. Thus, at 108, potential segments can be discarded due to exhibiting noise or otherwise lacking sufficient continuity with neighboring candidate segments. If a potential segment from 98 is spatially and temporally consistent with neighboring identified candidate segments (those considered as true activations at 96), the method can proceed to 102. At 102, the set of candidate segments identified at 96 can be combined with the set of segments identified at 100 as being spatially and temporally consistent with its neighboring segments.

At 104, a conduction pattern parameter (e.g., surrogate activation time parameter) can be identified (e.g., by conduction pattern identifier 32) for each candidate segment in the combined set of candidate segments. For example, the conduction pattern parameter provides a surrogate activation time, such as 50% of the amplitude of the downward sloping segment, such as disclosed herein or another location that can be consistently applied to the downward sloping segments. At 106, an output can be generated to display. For example, the output can include a sequence of activation snapshots in which the activation time can be displayed for different time indices, such as the graphical maps 120 shown in FIG. 6.

In the example of FIG. 6, the activation time can be demonstrated as a wave front or line pattern 122, 124, 126, 128, 130, 132 corresponding to activation times determined (e.g., by the method 90) for each of the plurality of points across the surface of a cardiac envelope (heart model) for each of a plurality of different time frames. Additionally, pre- and post-activation regions with respect to the activation time can further be visualized on the surface of the heart model according to a defined color scale, thereby bordering the identified activation time wave front on the surface. In other examples, the determined activation time may be shown in a single dynamic graphical map showing propagation of the wave front and associated pre and post regions across the heart model over at time interval.

Figure 7:
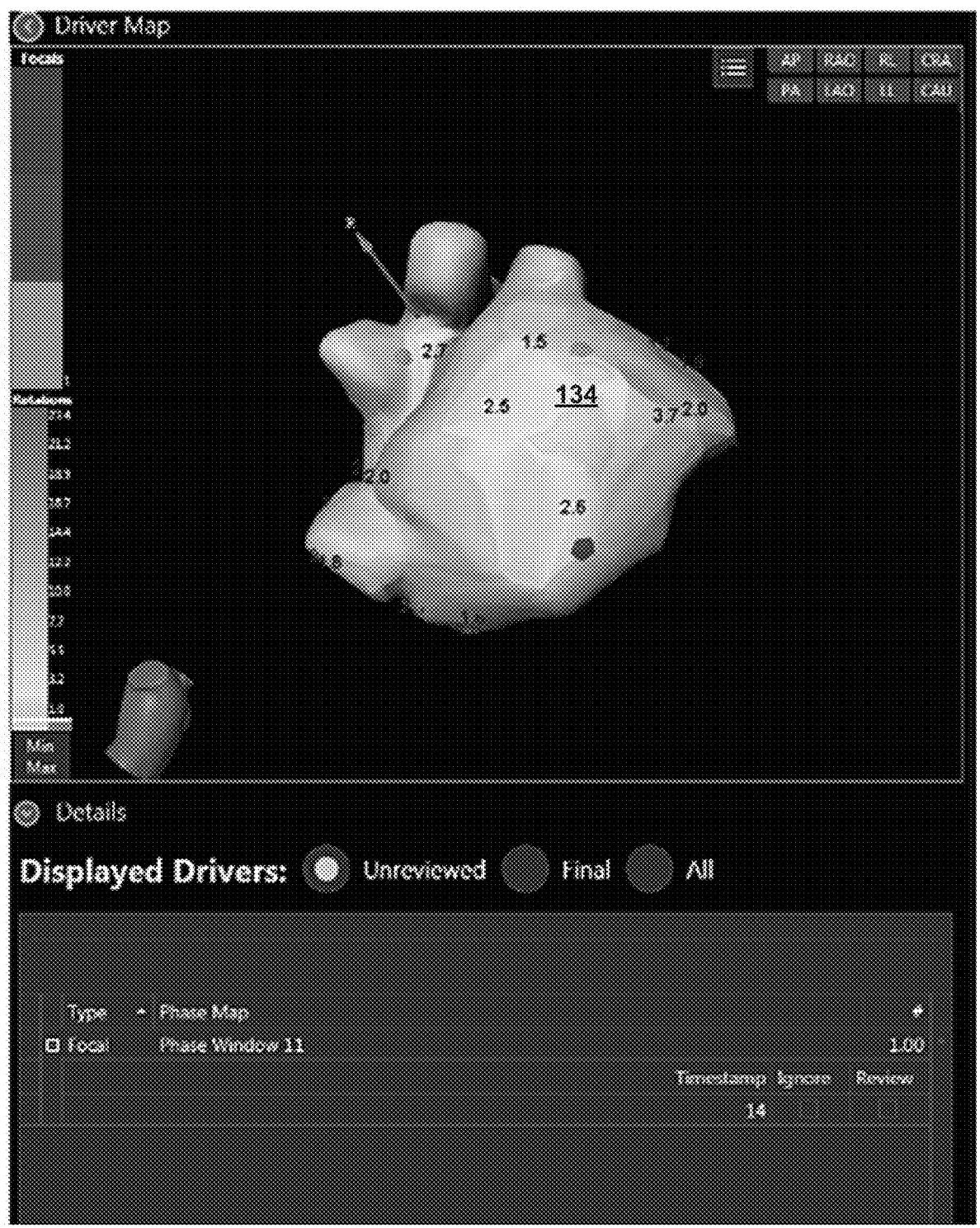
FIGS. 7 and 8 demonstrate examples of graphical maps that can be generated.

FIG. 7 depicts an example of a graphical map 134 of a heart in which a plurality of arrhythmogenic drivers are visualized on the heart by a corresponding color scale also superimposed on the heart map. In FIG. 7, the map includes an indication of the number of focal points that occur at corresponding focal regions across the surface of the heart model 134. A similar map can be generated based upon the number of focal points on the surface of the heart for any number of time stamps and can be displayed in a sequence (e.g., as a series of frames) to demonstrate the movement of focal points and changes.

Figure 8:
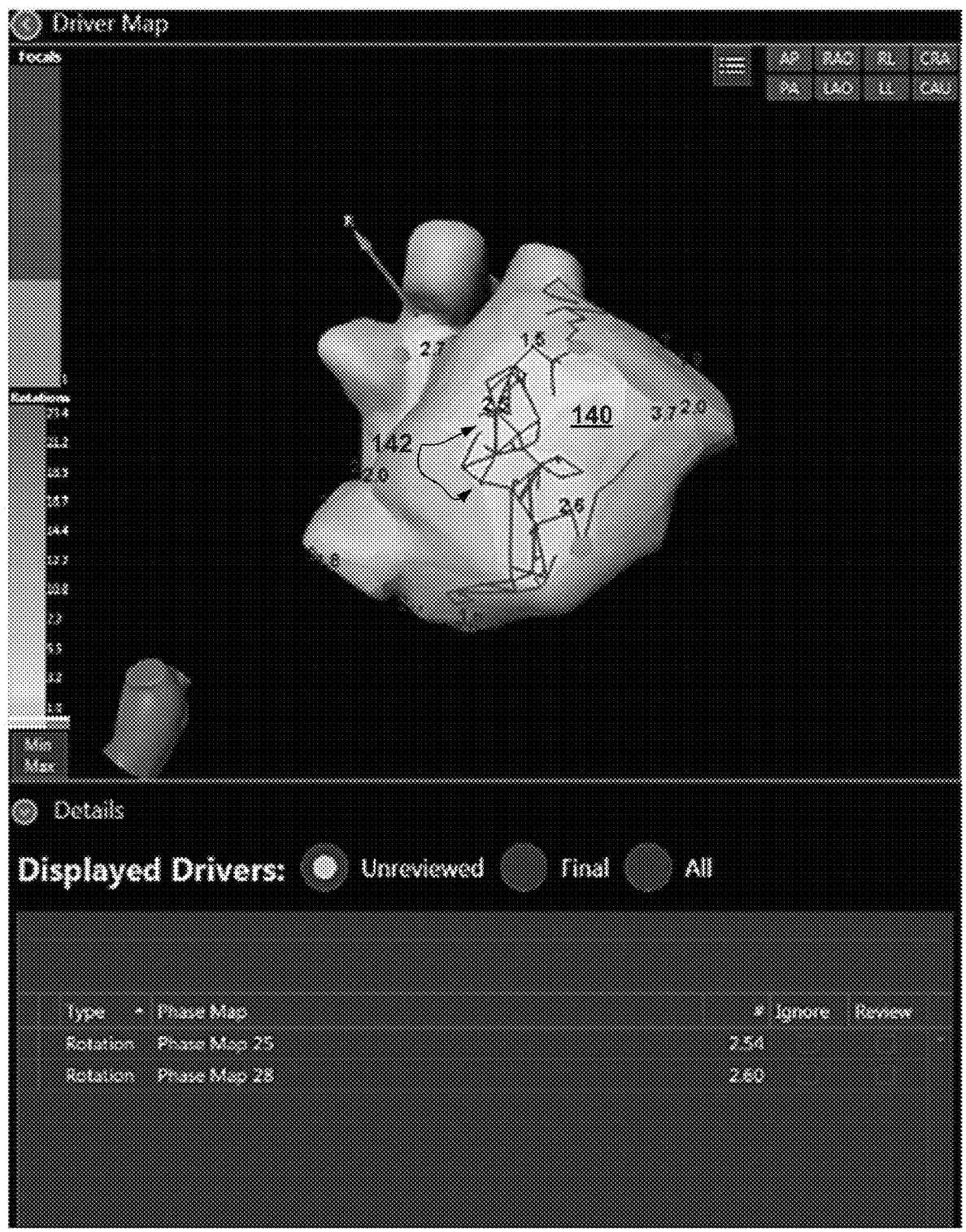

FIG. 8 depicts an example of another graphical map 140 of the heart demonstrating the number of rotational activities distributed across the surface. On the three-dimensional heart model also demonstrated are trajectory of rotors 142 across the surface over a selected time interval. The number of rotational activities for different regions across a heart are also indicated numerically in the graphical map that is generated.

In each of FIGS. 7 and 8, the GUI can be activated in response to a user input to document user review of each indication of the arrhythmogenic activity (e.g., rotational and/or focal activity) displayed in the graphical map 134, 140 or the GUI somewhere else, more generally. For instance, in response to a corresponding user input interacting with the displayed indication of arrhythmogenic activity (e.g., on the map of heart surface or an adjacent list) data can be stored in memory to document user review of each indication of the arrhythmogenic activity. In this way, user review can be facilitated as rotational activities and focal activities can be marked as reviewed or not reviewed.

Additionally, the GUI can enable a user to remove a given indication of the arrhythmogenic activity displayed in the graphical map in response to a user input. For example, a user can employ a user input device (e.g., mouse or touch screen interface) to reject one or more rotational activities or focal activities that are displayed on the map. The act of removal further can be tracked to document each instance of the user review and removal. Notes can also be provided and stored in memory if the user decides to document reasons for a decision to remove or retain the displayed indication of arrhythmogenic activity.

Figure 9:
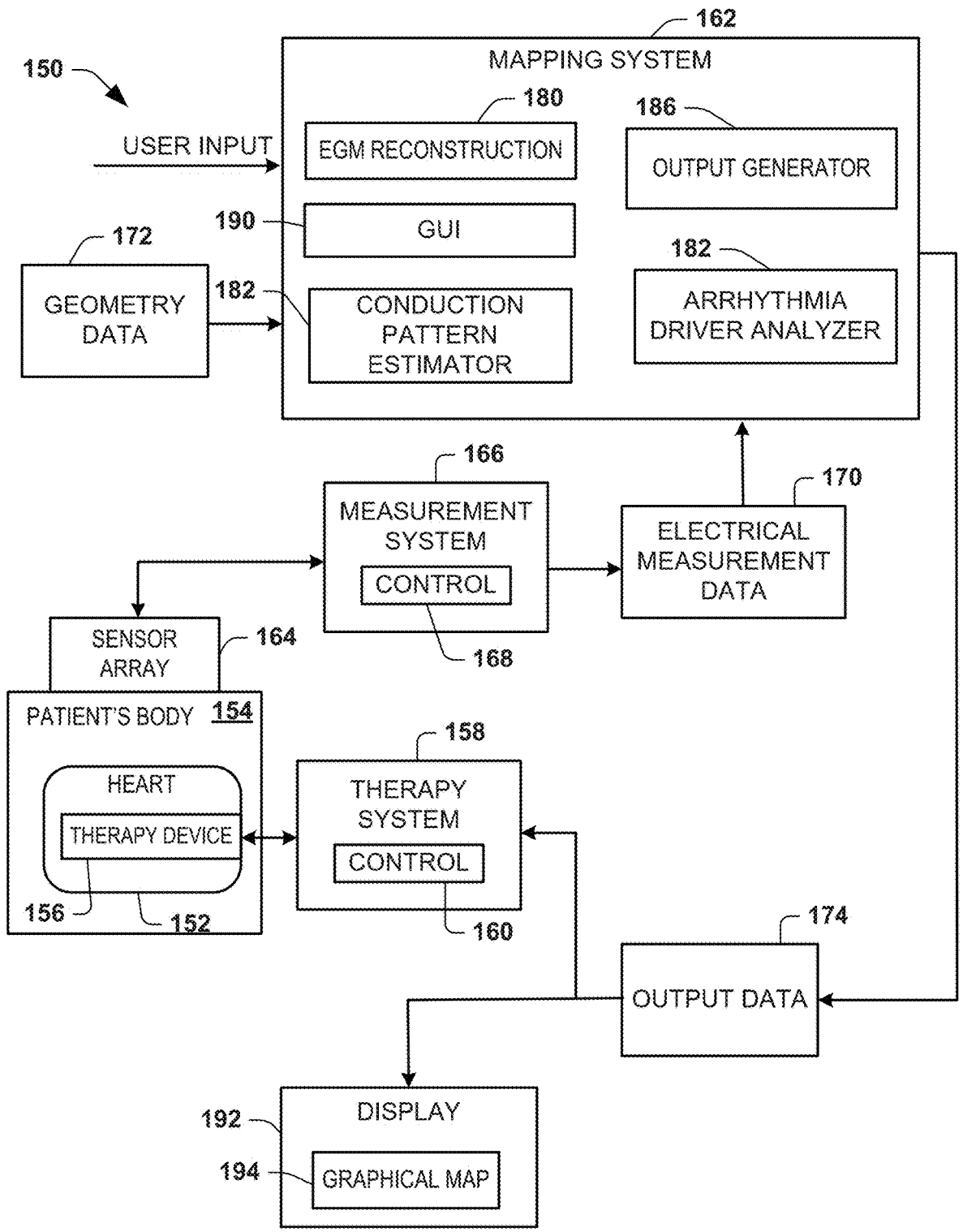
FIG. 9 depicts an example of a system to perform diagnostics and/or treatment with respect to a patient.

FIG. 9 depicts an example of a system 150 that can be utilized for performing diagnostics and/or treatment of a patient. In some examples, the system 150 can be implemented to generate corresponding maps for a patient's heart 152 in real time as part of a diagnostic procedure (e.g., an electrophysiology study) to help assess the electrical activity and identify arrhythmia drivers for the patient's heart. Additionally or alternatively, the system 150 can be utilized as part of a treatment procedure, such as to help a physician determine parameters for delivering a therapy to the patient (e.g., delivery location, amount and type of therapy) based on one or more identified arrhythmia drivers. For example, a catheter, such as a pacing or an ablation catheter, having one or more therapy delivery devices 156 affixed thereto can be inserted into a patient's body 154 as to contact the patient's heart 152, endocardially or epicardially. The placement of the therapy delivery device 156 can be guided according to the location of one or more arrhythmia drivers (e.g., stable rotational activity, foci, fast-firing locations or the like) that have been identified as disclosed herein. The guidance can be automated, semi-automated or be manually implemented based on information provided. Those skilled in the art will understand and appreciate various type and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof.

By way of example, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by a therapy system 158. Other types of therapy can also be delivered via the therapy system 158 and the invasive therapy delivery device 156 that is positioned within the body.

As a further example, the therapy system 158 can be located external to the patient's body 154 and be configured to control therapy that is being delivered by the device 156. For instance, the therapy system 158 includes controls (e.g., hardware and/or software) 160 that can communicate (e.g., supply) electrical signals via a conductive link electrically connected between the delivery device (e.g., one or more electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic) controls. One or more sensors (not shown) can also communicate sensor information back to the therapy system 158. The position of the device 156 relative to the heart 152 can be determined and tracked intraoperatively via an imaging modality (e.g., fluoroscopy, x-ray), a mapping system 162, direct vision or the like. The location of the device 156 and the therapy parameters thus can be combined to determine corresponding therapy parameter data.

Before, during and/or after delivering a therapy via the therapy system 158, another system or subsystem can be utilized to acquire electrophysiology information for the patient. In the example of FIG. 4, a sensor array 164 includes one or more electrodes that can be utilized for recording patient electrical activity. As one example, the sensor array 164 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which is incorporated herein by reference. Other arrangements and numbers of sensing electrodes can be used as the sensor array 164. As an example, the array can be a reduced set of electrodes, which does not cover the patient's entire torso and is designed for measuring electrical activity for a particular purpose (e.g., an array of electrodes specially designed for analyzing AF and/or VF) and/or for monitoring a predetermined spatial region of the heart.

One or more sensors may also be located on the device 156 that is inserted into the patient's body. Such sensors can be utilized separately or in conjunction with the non-invasive sensors 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensing, the sensor array(s) 164 provide the sensed electrical information to a corresponding measurement system 166. The measurement system 166 can include appropriate controls and signal processing circuitry 168 for providing corresponding measurement data 170 that describes electrical activity detected by the sensors in the sensor array 164. The measurement data 170 can include analog and/or digital information (e.g., corresponding to electrical data 59).

The control 168 can also be configured to control the data acquisition process (e.g., sample rate, line filtering) for measuring electrical activity and providing the measurement data 170. In some examples, the control 168 can control acquisition of measurement data 170 separately from the therapy system operation, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 170 and therapy parameters use to deliver therapy as to facilitate the evaluation and analysis thereof.

Since the measurement system 166 can measure electrical activity of a predetermined region or the entire heart concurrently (e.g., where the sensor array 164 covers the entire thorax of the patient's body 154), the resulting output data (e.g., visualizing attributes of identified conduction patterns, such as rotational activity and/or other electrocardiographic maps) thus can also represent concurrent data for the predetermined region or the entire heart in a temporally and spatially consistent manner. The time interval for which the output data/maps are computed can be selected based on user input (e.g., selecting a timer interval from one or more waveforms). Additionally or alternatively, the selected intervals can be synchronized with the application of therapy by the therapy system 158.

For the example where the electrical measurement data is obtained non-invasively (e.g., via body surface sensor array 164), electrogram reconstruction 180 can be programmed to compute an inverse solution and provide corresponding reconstructed electrograms based on the process signals and the geometry data 172. The reconstructed electrograms thus can correspond to electrocardiographic activity across a cardiac envelope, and can include static (three-dimensional at a given instant in time) and/or be dynamic (e.g., four-dimensional map that varies over one or more time intervals). Examples of inverse algorithms that can be utilized in the system 10 include those disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations on a cardiac envelope (e.g., greater than 1000 locations, such as about 2000 locations or more). In some examples, the mapping system 162 can compute electrical activity over a sub-region of the heart based on electrical activity measured invasively, such as via a basket catheter or other form of measurement probe.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed generic model or a combination thereof (e.g., a model that is modified based on patient anatomy).

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

Following (or concurrently with) determining electrical potential data (e.g., electrogram data computed from non-invasively acquired measurements) across the geometric surface of the heart 152, a conduction pattern estimator 182 can process one or more intervals of the electrogram data to determine activation time across the surface. The conduction pattern estimator 182 constitutes instructions, which can be implemented according to any of the approaches disclosed herein (see, e.g., FIGS. 1-6 and corresponding description), and thus can provide activation times for each of the plurality of signals represented by the electrogram data. The activation times can be aggregated with geometry data to provide output data 174 to a display 192 for visualizing a graphical activation map (see, e.g., FIG. 6) 194 depicting a wave front and propagation thereof across the heart surface based on the identified conduction patterns for such surface over one or more time intervals.

The mapping system 162 can also include an automated arrhythmia driver analyzer method 182 to identify one or more drivers of cardiac arrhythmia, such as disclosed herein (e.g., corresponding to arrhythmogenic activity calculator 34). The arrhythmia driver analyzer 182 can also be programmed to compute other characteristics associated with each identified arrhythmia driver, such as including driver sustainability, trajectories of the rotational activity, wave front lines, rotation count for of the rotational activity, rotation direction for of the rotational activity, angular velocity for of the rotational activity, connectivity between rotating cores, cycle length and related statistics associated therewith.

The mapping system 162 is programmed to combine the measurement data 170 corresponding to electrical activity of the heart 152 with geometry data 172 (e.g., corresponding to geometry data 57) by applying appropriate processing and computations to provide corresponding output data 174. The output data 174 can include data provided to the display 192 for visualization of one or more graphical maps 194 and other related information to characterize one or more arrhythmia drivers, which can be localized or global drivers across the cardiac envelope (e.g., on a surface of the heart 152).

The output generator (e.g., output engine 36) 186 can be programmed to generate graphic maps based on the computed output data, such as noted above. Parameters associated with the displayed graphical representation, corresponding to an output visualization of the computed map, such as including selecting a time interval, a type of information that is to be presented in the visualization and the like can be selected in response to a user input via a graphical user interface (GUI) 190. For example, a user can employ the GUI 190 to selectively program one or more parameters (e.g., temporal and spatial thresholds, filter parameters and the like) utilized by the arrhythmia driver analyzer method 182 and/or to select one or more sample time intervals to set a time duration for the electrical data 170 that is utilized by the mapping system 162. The mapping system 162 thus can generate corresponding output data 174 that can in turn be rendered by the output engine 186 as a corresponding graphical output in a display 192, such as including an electrocardiographic map 194. For example, the map generator can generate maps and other output visualizations, such as including but not limited to the maps and other output visualizations disclosed herein.

Additionally, in some examples, the output data 174 can be utilized by the therapy system 158. The control that is implemented can be fully automated control, semi-automated control (partially automated and responsive to a user input) or manual control based on the output data 174. In some examples, the control 160 of the therapy system can utilize the output data 174 to control one or more therapy parameters. As an example, the control 160 can control delivery of ablation therapy to a site of the heart (e.g., epicardial or endocardial wall) based on activation timing or activation wave fronts determined by the conduction pattern estimator 182 and/or based on one or more arrhythmia drivers identified by the arrhythmia driver analyzer method 182. In other examples, an individual can view the map 194 generated in the display to manually control the therapy system. Other types of therapy and devices can also be controlled based on the output data 174 and corresponding graphical map 194.

In view of the foregoing, it is understood that certain systems methods disclosed herein utilize the spatial continuity of a true activation to differentiate the noise. As mentioned above, the use of filters to remove noise may also distort signal and activation detection. Thus, instead of using filter, systems and methods disclosed herein can identify and remove noise-related detections based on its lack of spatial footprint (i.e., no continuous activation from or towards its spatial neighbors). Since this approach does not rely on filters, it avoids the creation of artifacts due to filters, and largely maintains the correct timing and morphology of the downward slopes, where the activation happens and is detected.

Since this approach does not require the calculation of phase within a cycle before the detection of activation, a shorter time interval for data can now be processed, thereby reducing computational requirements. As a result, the visualization of such data is more focused on the wave front instead of the entire cycle, which focuses the understanding of conduction. In summary, the systems and methods herein (1) avoid signal distortion due to filtering, (2) use a new and more robust way to pick the activation time, (3) do not require phase calculation and is thus capable of analyzing data with shorter duration, and (4) enable a new and easy-to-understand visualization mode for the activation wave front.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method, comprising:
   analyzing, by one or more processors, a morphology and an amplitude of each of a plurality of electrophysiological signals captured by a plurality of sensors distributed across a surface of a patient's body to identify candidate segments of each signal satisfying predetermined conduction pattern criteria;
   determining, by the one or more processors, a conduction timing parameter for each candidate segment in each of the electrophysiological signals; and
   causing, by the one or more processors, a graphical map to be outputted on a display that includes a visualization of or derived based on the conduction timing parameters determined for the plurality of electrophysiological signals.

2. The method of claim 1, wherein analyzing the morphology and the amplitude further comprises determining a set of potential segments in each of the electrophysiological signals satisfying downward slope criteria.

3. The method of claim 2, wherein determining the set of potential segments further comprises:
   selecting at least a portion of the candidate segments from the set of potential segments based on the amplitude and duration thereof satisfying amplitude and duration criteria; and
   designating a portion from the set of potential segments for further evaluation.

4. The method of claim 3, wherein the further evaluation comprises:
   selecting, as one of the candidate segments, each segment in the set of potential segments that is spatially and temporally consistent with neighboring candidates that have been selected and aggregating the candidate segments for each of the plurality of electrophysiological signals; and
   removing each respective segment from further consideration in determining the conduction timing parameter that is not spatially and/or temporally consistent with neighboring candidates that have been selected.

5. The method of claim 1, further comprising:
   acquiring electrical signals by a non-invasive arrangement of the plurality of sensors distributed on an outer body surface of the patient; and
   computing reconstructed electrical signals on a cardiac envelope with respect to an anatomical surface of the patient's heart based on the acquired electrical signals and geometry data describing spatial locations of the plurality of sensors with respect to patient geometry that includes the anatomical surface of the patient's heart.

6. The method of claim 1, wherein the method further comprises:
   computing an indication of arrhythmogenic activity based on the conduction timing parameter;
   generating the graphical map to visualize the indication of arrhythmogenic activity with respect to the heart; and
   outputting the graphical map to a display device.

7. The method of claim 6, wherein the indication of arrhythmogenic activity comprises a number of focal points, a number of rotational activities and/or a trajectory of at least one rotational activity, the indication of arrhythmogenic activity being displayed in the graphical map spatially with respect to the heart.

8. The method of claim 6, further comprising storing data to document user review of each indication of arrhythmogenic activity displayed in the graphical map in response to a corresponding user input interacting with the displayed indication of arrhythmogenic activity.

9. The method of claim 6, further comprising:
   removing a given indication of arrhythmogenic activity displayed in the graphical map in response to a user input instruction to reject the given indication of arrhythmogenic activity; and
   storing, in memory, data documenting the user input instruction.

10. The method of claim 1, wherein the conduction timing parameter is an activation time computed for each of a plurality of points on the surface over at least one time interval.

11. The method of claim 10, the method further comprising:

selecting one of a plurality of different activation time calculating functions based on at least one of noise, amplitude and morphology of the signals, the selected one of the activation time calculating functions performing the analyzing to identify the candidate segments; and using the selected activation time calculating function to compute the conduction timing parameter as an activation time for the electrophysiological signals.

12. A system comprising:

memory to store machine readable instructions and data, the data comprising electrical data representing electrophysiological signals distributed across a body surface;

at least one processor to access the memory and execute the instructions, the instructions comprising:

a conduction pattern estimator that analyzes at least a morphology that includes a downward slope of each of a plurality of electrophysiological signals across a surface of a patient's body, to identify candidate segments of each of the plurality of electrophysiological signals that satisfy predetermined conduction pattern criteria;

a conduction pattern parameter identifier that determines a conduction timing parameter for each of the identified candidate segments in the electrophysiological signals; and an output engine that provides output data to drive a display with a graphical map that includes a visualization of or derived based on the conduction timing parameters determined for the electrophysiological signals.

13. The system of claim 12, wherein the conduction pattern estimator is further programmed to:

determine a set of potential segments in each of the electrophysiological signals satisfying downward slope criteria;

select at least a portion of the candidate segments from the set of potential segments based on an amplitude and duration thereof satisfying amplitude and duration criteria; and designate another portion from the set of potential segments as questionable candidate segments for further evaluation.

14. The system of claim 13, wherein the conduction pattern estimator is further programmed to:

select, as one of the candidate segments, each segment in the set of potential segments that is spatially and temporally consistent with neighboring candidates that have been selected and aggregating the candidate segments for each of the plurality of electrophysiological signals; and removing each respective segment from further consideration in determining the conduction timing parameter that is not spatially and/or temporally consistent with neighboring candidates that have been selected.

15. The system of claim 12, wherein the conduction timing parameter is an activation time parameter, the further comprises locating an activation time on the downward slope of each of the candidate segments.

16. The system of claim 15, further comprising a dynamic activation time estimator that selects one of a plurality of different activation time calculating functions based on at least one of a noise, an amplitude and the morphology of the electrophysiological signals, the selected one of the activation time calculating functions analyzing the signal segments to identify the candidate segments; and the conduction pattern estimator including a signal segment analyzer that employs the selected activation time calculating function to determine the activation time for each of the electrophysiological signals.

17. The system of claim 12, further comprising an arrhythmogenic activity calculator that computes an indication of arrhythmogenic activity based on the conduction timing parameter determined for the electrophysiological signals, wherein the output engine generates the graphical map to visualize the indication of arrhythmogenic activity with respect to the heart.

18. The system of claim 17, wherein the indication of arrhythmogenic activity comprises a number of focal points, a number of rotational activities and/or a trajectory of at least one rotational activity, the indication of arrhythmogenic activity being displayed in the graphical map spatially with respect to the heart.

19. The system of claim 17, further comprising a user interface that stores user data in the memory to document user review of each indication of arrhythmogenic activity displayed in the graphical map in response to a corresponding user input interacting with the displayed indication of arrhythmogenic activity, wherein the user interface modifies the stored user data to remove a given indication of arrhythmogenic activity displayed in the graphical map in response to a user input instruction to reject the given indication of arrhythmogenic activity.

20. The system of claim 12, further comprising a signal segment detector that determines slope and peaks for each of the plurality of electrophysiological signals, the signal segment detector identifying downward sloping signal segments based on the determined slope and peaks.

21. The system of claim 12, further comprising:

a non-invasive arrangement of sensors distributed on an outer body surface of the patient to acquire electrical signals from a plurality of locations on the outer body surface; and computing reconstructed electrical signals on a cardiac envelope with respect to an anatomical surface of the heart based on the acquired electrical signals and geometry data describing spatial locations of the sensors with respect to the patient geometry that includes the anatomical surface of the heart, the reconstructed electrical signals being stored in the memory as the plurality of electrophysiological signals.

* * * * *